(12) United States Patent
Ushakov et al.

(10) Patent No.: US 11,891,557 B2
(45) Date of Patent: *Feb. 6, 2024

(54) ISOTHIOCYANATO TOLANE DERIVATIVES

(71) Applicant: MERCK PATENT GMBH, Darmstadt (DE)

(72) Inventors: Dmitry Ushakov, Muenster (DE); Beate Schneider, Seeheim-Jugenheim (DE); Carsten Fritzsch, Darmstadt (DE); Michael Wittek, Erzhausen (DE); Dagmar Klass, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/647,181

(22) PCT Filed: Sep. 11, 2018

(86) PCT No.: PCT/EP2018/074365
§ 371 (c)(1),
(2) Date: Mar. 13, 2020

(87) PCT Pub. No.: WO2019/052972
PCT Pub. Date: Mar. 21, 2019

(65) Prior Publication Data
US 2021/0122977 A1    Apr. 29, 2021

(30) Foreign Application Priority Data

Sep. 14, 2017 (EP) .................................. 17191016

(51) Int. Cl.
| | |
|---|---|
| *C09K 19/18* | (2006.01) |
| *C07C 15/54* | (2006.01) |
| *C07C 331/28* | (2006.01) |
| *C07C 25/24* | (2006.01) |

(52) U.S. Cl.
CPC .............. *C09K 19/18* (2013.01); *C07C 15/54* (2013.01); *C07C 25/24* (2013.01); *C07C 331/28* (2013.01); *C09K 2019/181* (2013.01); *C09K 2219/11* (2013.01)

(58) Field of Classification Search
CPC .............. C09K 19/18; C09K 2019/181; C07C 15/54; C07C 25/24; C07C 331/28
See application file for complete search history.

(56) References Cited

U.S. PATENT DOCUMENTS

| | | | |
|---|---|---|---|
| 7,361,288 B2 | 4/2008 | Lüssem et al. | |
| 8,999,198 B2* | 4/2015 | Reiffenrath | C09K 19/08 |
| | | | 252/299.63 |
| 9,169,438 B2* | 10/2015 | Reiffenrath | C07C 25/24 |
| 9,175,219 B2* | 11/2015 | Jasper | C09K 19/322 |
| 9,777,217 B2* | 10/2017 | Jasper | C07C 331/08 |
| 10,017,695 B2 | 7/2018 | Lietzau et al. | |
| 10,099,975 B2* | 10/2018 | Jasper | C09K 19/32 |
| 10,711,195 B2* | 7/2020 | Manabe | C09K 19/3458 |
| 11,261,163 B2* | 3/2022 | Bremer | C07D 239/28 |
| 11,268,026 B2* | 3/2022 | Klass | C09K 19/3003 |
| 11,306,251 B2* | 4/2022 | Klass | C09K 19/3059 |
| 2013/0207038 A1 | 8/2013 | Haensel et al. | |
| 2018/0337445 A1* | 11/2018 | Sullivan | C09K 19/18 |

FOREIGN PATENT DOCUMENTS

| | | | |
|---|---|---|---|
| CN | 106398714 A | * | 2/2017 |
| CN | 106699710 B | | 8/2019 |
| DE | 102004029429 A1 | | 2/2005 |
| EP | 2628779 B1 | | 5/2017 |
| EP | 3085753 B1 | | 4/2019 |
| JP | 10236992 A | | 9/1998 |

OTHER PUBLICATIONS

English translation of CN106398714. (Year: 2017).*
Dabrowski et al., "High Birefringent Liquid Crystalline Materials", 2008, IDRC, 08, 35-38. (Year: 2008).*
Hsu et al., "Synthesis of laterally substituted bistolane liquid crystals", 2000, Liquid Crystals, vol. 27 No. 2, 283-287. (Year: 2000).*
M. Tobisu et al., 'Palladium(II)-catalyzed synthesis of dibenzothiophene derivatives via the cleavage of carbon-sulfur and carbon-hydrogen bonds', Chem. Sci. 2016, 7, 2587-2591.
International Search Report PCT/EP2018/074365 dated Oct. 29, 2018 pp. (1-3).

* cited by examiner

*Primary Examiner* — Chanceity N Robinson
*Assistant Examiner* — Anna Malloy
(74) *Attorney, Agent, or Firm* — MILLEN, WHITE, ZELANO & BRANIGAN, P.C.; Jennifer J. Branigan

(57) ABSTRACT

Isothiocyanato tolane derivatives of formula I-1

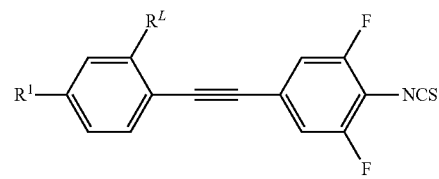

and liquid-crystalline media comprising same are suitable for use in high-frequency components, especially microwave components for high-frequency devices, such as devices for shifting the phase of microwaves, in particular for microwave phased-array antennas.

14 Claims, No Drawings

ISOTHIOCYANATO TOLANE DERIVATIVES

The present invention relates to isothiocyanato tolane derivatives, to liquid-crystalline media comprising same and to high-frequency components comprising these media, especially microwave components for high-frequency devices, such as devices for shifting the phase of microwaves, tunable filters, tunable metamaterial structures, and electronic beam steering antennas (e.g. phased array antennas).

Liquid-crystalline media have a been used for many years in electro-optical displays (liquid crystal displays: LCDs) in order to display information.

Recently, liquid-crystalline media have also been proposed for use in components for microwave technology, such as, for example, in DE 10 2004 029 429 A and in JP 2005-120208 (A).

An industrially valuable application of liquid-crystalline media in high-frequency technology is based on their property that their dielectric properties can be controlled, particularly for the gigahertz range, by a variable voltage. This enables the construction of tunable antennae which do not contain any moving parts (A. Gaebler, A. Moessinger, F. Goelden, et al., "Liquid Crystal-Reconfigurable Antenna Concepts for Space Applications at Microwave and Millimeter Waves", International Journal of Antennas and Propagation, Vol. 2009 (2009), article ID 876989, 7 pages, doi: 10.1155/2009/876989).

A. Penirschke, S. Müller, P. Scheele, C. Weil, M. Wittek, C. Hock and R. Jakoby: "Cavity Perturbation Method for Characterization of Liquid Crystals up to 35 GHz", $34^{th}$ European Microwave Conference—Amsterdam, pp. 545-548, describe, inter alia, the properties of the known single liquid-crystalline substance K15 (Merck KGaA, Germany) at a frequency of 9 GHz.

In JP 2002003844 A compounds having a terminal NCS group, for example of the following formula

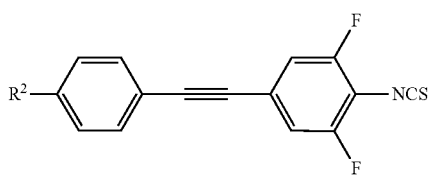

where $R^1$ for example denotes alkyl, are described for the use in liquid-crystal media for display applications. The use of such compounds has been proposed for components for high-frequency technology in DE 10 2004 029429 A1.

However, the compositions or individual compounds known to date are generally afflicted with disadvantages. Most of them result, besides other deficiencies, in disadvantageously high losses, inadequate phase shifts or low tunability, resulting in inadequate material quality.

Development in the area of liquid-crystalline materials for the use in microwave applications is far from complete. In order to improve the properties of microwave devices, attempts are constantly being made to develop novel compounds which enable such devices to be optimised. For use in high-frequency technology, liquid-crystalline media having particular, hitherto rather unusual, uncommon properties, or combinations of properties, are required.

Novel components for liquid-crystalline media having improved properties are thus necessary. In particular, the loss in the microwave range must be reduced and the material quality (η) improved.

In addition, there is a demand for an improvement in the low-temperature behaviour of the components. An improvement in both the operating properties and also in the shelf life is necessary here.

Thus, there is a considerable demand for liquid-crystalline media having suitable properties for corresponding practical applications.

An object of the present invention is to provide compounds having advantageous properties for use in liquid-crystalline media for the use in components for microwave applications.

Surprisingly, it has now been found that it is possible, using the compounds according to the invention, to achieve liquid-crystalline media having a suitable, nematic phase range and high Δn, low dielectric loss, high tunability and high material quality, which do not have the disadvantages of the prior-art materials, or at least only do so to a considerably reduced extent.

The object of the invention is achieved by compounds of the general formula I

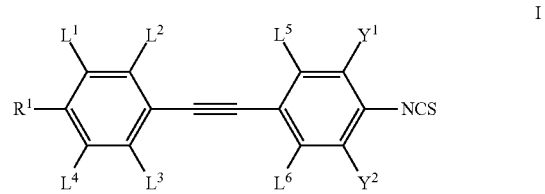

in which $R^1$ denotes an alkyl or alkoxy radical having 1 to 15 C atoms, where, in addition, one or more $CH_2$ groups in these radicals may each be replaced, independently of one another, by —C≡C—, —$CF_2$O—, —O$CF_2$—, —CH=CH—,

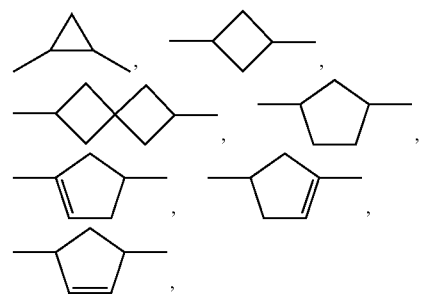

—O—, —CO—O— or —O—CO— in such a way that O atoms are not linked directly to one another, and in which, in addition, one or more H atoms may be replaced by halogen, $L^1$, $L^2$, $L^3$, $L^4$, $L^5$ and $L^6$ independently of one another, denote H, F, Cl, $CF_3$ or $R^L$, where at least one of the groups $L^1$, $L^2$, $L^3$ and $L^4$ denotes $R^L$, $R^L$ on each occurrence, identically or differently, denotes alkyl, alkoxy, alkenyl, alkenyloxy or alkoxyalkyl, each having up 10 C atoms, or cycloalkyl or cycloalkenyl having up to 7 C atoms or alkylcycloalkyl, alkylcycloalkenyl, alkenylcycloalkyl or alkenylcycloalkenyl having up to 10 C atoms, Y$^1$ and Y$^2$ denote, independently of one another, H, F or Cl.

The compounds according to the invention have a comparatively very low melting point, a suitably high clearing point, high optical anisotropy (Δn) and clearly positive dielectric anisotropy, making them particularly suitable for use in the gigahertz region. The relatively low loss factor in the microwave spectrum is advantageous. The compounds have, alone or in a mixture with further mesogenic components, a nematic phase over a broad temperature range. The totality of these properties make them particularly suitable for use in components and devices for high-frequency technology, in particular devices for shifting the phase of microwaves, tunable filters, tunable metamaterial structures, and electronic beam steering antennas (e.g. phased array antennas). Liquid-crystalline media according to the invention have the corresponding properties.

A further object of the present invention is to provide liquid-crystalline media suitable for applications in the microwave range, in particular for phase shifters or LC based antenna elements or tunable filters in the micro wave (MW) region.

A further object of the present invention are components operable in the microwave region of the electromagnetic spectrum and devices comprising said components.

Preferred components are phase shifters, varactors, wireless and radio wave antenna arrays, matching circuits, adaptive filters and others.

If R$^1$ is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

R$^1$ may be an alkenyl radical having from 2 to 15 carbon atoms, which may be straight-chain or branched. It is preferably straight-chain and has from 2 to 7 carbon atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl.

R$^1$ may be oxaalkyl, preferably straight-chain 2-oxapropyl (=methoxymethyl), 2-oxabutyl (=ethoxymethyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl.

R$^1$ may be an alkyl radical having from 1 to 15 carbon atoms in which one CH$_2$ group has been replaced by —O— and one has been replaced by —CO—, where these are preferably adjacent. This thus contains an acyloxy group —CO—O— or an oxycarbonyl group —O—CO—. This is preferably straight-chain and has from 2 to 6 carbon atoms.

R$^1$ may be an alkyl radical having from 1 to 15 carbon atoms in which one CH$_2$ group has been replaced by unsubstituted or substituted —CH=CH— and an adjacent CH$_2$ group has been replaced by CO or CO—O or O—CO, where this may be straight-chain or branched. It is preferably straight-chain and has from 4 to 13 carbon atoms.

R$^1$ may be an alkyl radical having from 1 to 15 carbon atoms or alkenyl radical having from 2 to 15 carbon atoms, each of which is monosubstituted by —CN or —CF$_3$ and is preferably straight-chain. The substitution by —CN or —CF$_3$ is possible in any desired position.

R$^1$ may be an alkyl radical in which two or more CH$_2$ groups have been replaced by —O— and/or —CO—O—, where this may be straight-chain or branched. It is preferably branched and has from 3 to 12 carbon atoms.

R$^1$ may be an alkyl radical having from 1 to 15 carbon atoms or an alkenyl radical having from 2 to 15 carbon atoms, each of which is at least monosubstituted by halogen (F, Cl, Br, I), where these radicals are preferably straight-chain and halogen is preferably —F or —Cl. In the case of polysubstitution, halogen is preferably —F. The resultant radicals also include perfluorinated radicals, such as —CF$_3$. In the case of monosubstitution, the fluorine or chlorine substituent can be in any desired position, but is preferably in the w-position.

R$^1$ may be an alkyl or alkoxy radical having 1 to 15 C atoms, preferably 1 to 5, particularly preferably 1, where one or more CH$_2$ groups, preferably one, in these radicals may each be replaced, independently of one another, by

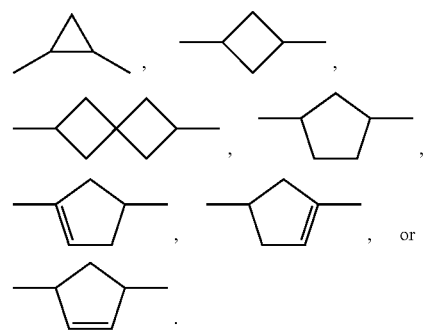

R$^1$ is preferably cyclopropyl, cyclobutyl, cyclopentyl or cyclopent-1-enyl.

In formula I, preferably L$^5$ and L$^6$ both denote H, Y$^1$ denotes Fund Y$^2$ denotes H or F, particularly preferably F.

In another preferred embodiment, one of L$^1$, L$^2$, L$^3$ and L$^4$ denotes F.

The compounds of formula I are particularly preferably selected from the group of compounds of the following sub-formulae:

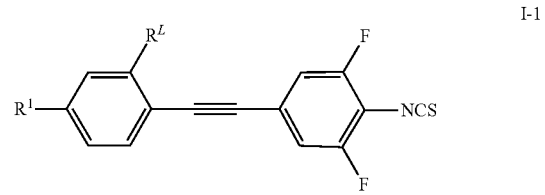

I-1

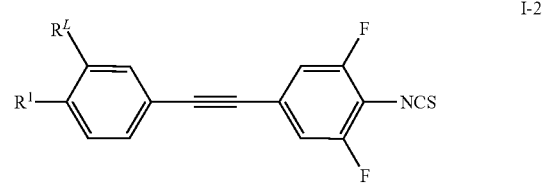

I-2

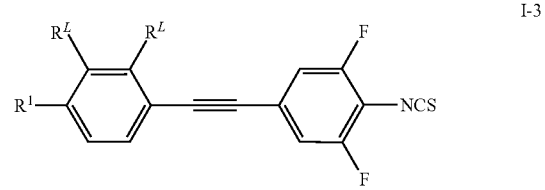

I-3

I-4
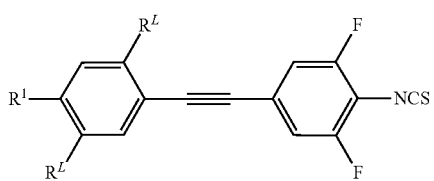

I-5
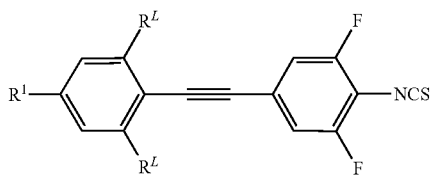

I-6
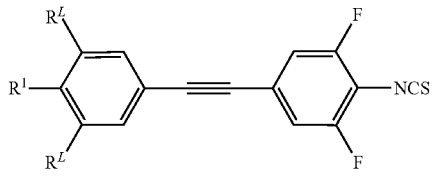

I-7
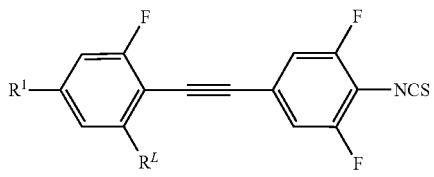

I-8
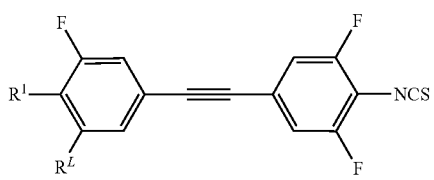

I-9
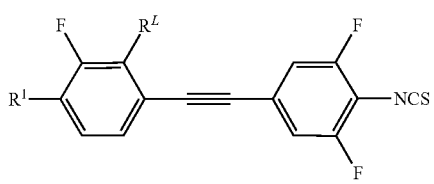

I-10
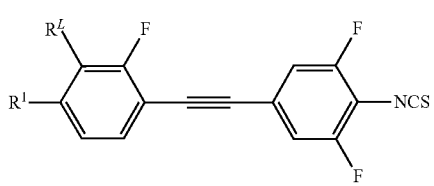

I-11
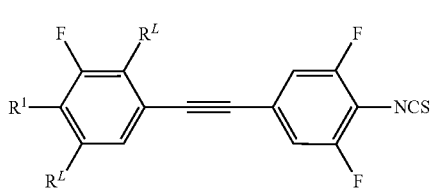

I-12
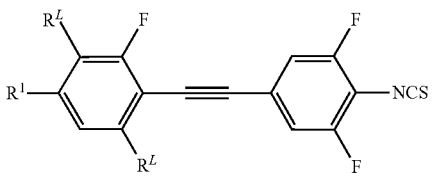

in which $R^1$ has the meaning given above and preferably denotes alkyl or alkenyl having up to 7 C atoms, particularly preferably ethyl, n-propyl, n-butyl or n-pentyl, n-hexyl, $R^L$ on each occurrence, the same or differently, denotes alkyl or alkenyl having 1 to 5 C atoms, or cycloalkyl or cycloalkenyl each having 3 to 6 C atoms, preferably methyl, ethyl, n-propyl, n-butyl, isopropyl, cyclopropyl, cyclobutyl, cyclopentyl or cyclopent-1-enyl.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for the said reactions. Use can be made here of variants which are known per se, but are not mentioned here in greater detail. If desired, the starting materials can also be formed in situ by not isolating them from the reaction mixture, but instead immediately converting them further into the compounds of the general formula I Preferred synthetic pathways towards compounds according to the invention is shown in the scheme below and is further illustrated by means of the working examples. The syntheses can be adapted to the respective desired compounds of the general formula I by choice of suitable starting materials.

Scheme 1

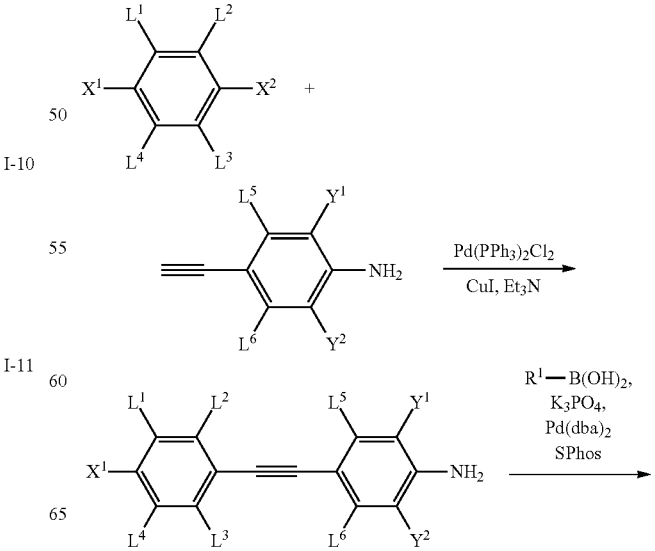

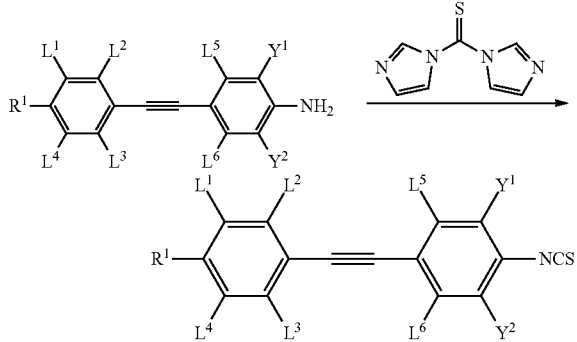

In scheme 1, the groups have the meanings defined in claim 1, and $X^1$ and $X^2$ denote a leaving group. Examples of leaving groups are, Cl, Br, I, and sulfonate such as tosylate, mesylate, trifluoromethane sulfonate, nosylate, and the like. $X^1$ and $X^2$ can be the same or different, preferably different. Particularly preferably, $X^1$ or $X^2$ denotes Br ad the other of $X^1$ and $X^2$ denotes I.

Another object of the present invention is a compound of formula I*

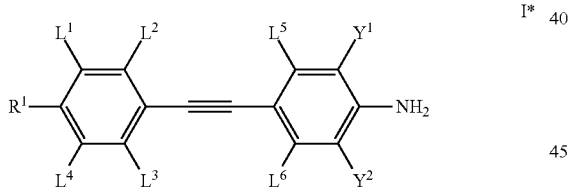

in which the occurring groups have the meanings indicated above for formula I.

Another object of the present invention is a process for the preparation of a compound of formula I in which a compound of formula I* is transferred into a compound of formula I. Preferred reagents for the process according to the invention are carbon disulfide, thiophosgene, thiocarbonyl diimidazole, di-2-pyridyl thionocarbonate, bis(dimethylthiocarbamoyl) disulfide, dimethylthiocarbamoyl chloride and phenyl chlorothionoformate.

The reactions described should only be regarded as illustrative. The person skilled in the art can carry out corresponding variations of the syntheses described and also follow other suitable synthetic routes in order to obtain compounds of the formula I.

As already mentioned, the compounds of the general formula I can be used in liquid-crystalline media.

The present invention therefore also relates to a liquid-crystalline medium comprising two or more liquid-crystalline compounds, comprising one or more compounds of the general formula I.

The liquid-crystalline media in accordance with the present invention comprise one or more compounds of the formula I and optionally at least one further, preferably mesogenic compound. The liquid-crystal medium therefore preferably comprises two or more compounds which are preferably liquid-crystalline. Preferred media comprise the preferred compounds of the formula I.

Further components of the liquid-crystalline media are preferably selected from the compounds of the formula II:

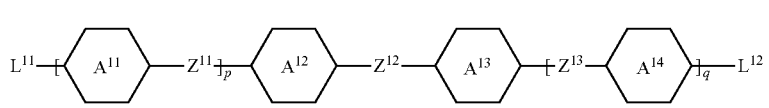

in which $L^{11}$ denotes $R^{11}$ or $X^{11}$, $L^{12}$ denotes $R^{12}$ or $X^{12}$, $R^{11}$ and $R^{12}$, independently of one another, denote unfluorinated alkyl or unfluorinated alkoxy having 1 to 17, preferably having 3 to 10, C atoms or unfluorinated alkenyl, unfluorinated alkynyl, unfluorinated alkenyloxy or unfluorinated alkoxyalkyl having 2 to 15, preferably 3 to 10, C atoms, preferably alkyl or unfluorinated alkenyl, $X^{11}$ and $X^{12}$, independently of one another, denote F, Cl, Br, —CN, —NCS, —SCN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably $CF_3$, $OCF_3$, Cl, F or NCS, p, q, independently of one another, denote 0 or 1, $Z^{11}$ to $Z^{13}$, independently of one another, denote trans-CH=CH—, trans-CF=CF—, —C≡C— or a single bond,

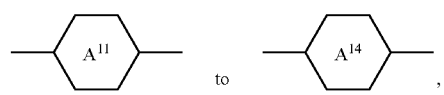

independently of one another, denote

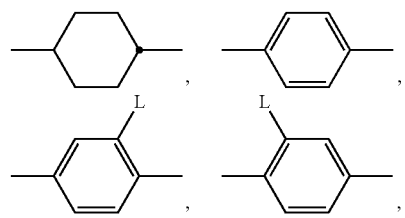

-continued

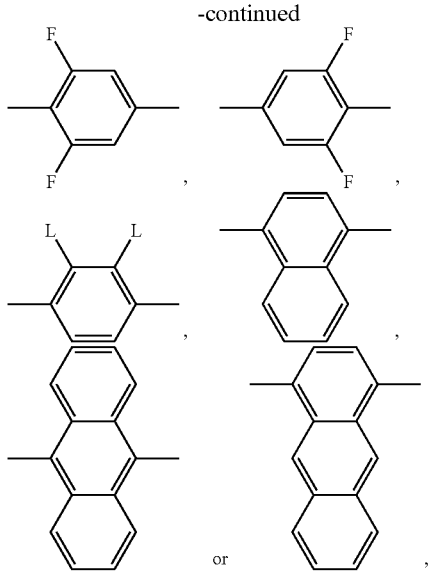

and

L on each occurrence, independently of one another, denotes branched or unbranched alkyl, alkenyl or alkynyl having 1 to 12 C atoms, in which, independently of one another, one or more "—$CH_2$—" groups may also be replaced by O, or denotes $C_3$-$C_6$ cycloalkyl, $C_3$-$C_6$ cycloalkenyl, fluorinated alkyl or alkenyl, fluorinated alkoxy or alkenyloxy, F, Cl, Br, CN, NCS, SCN or $SF_5$.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.005 to 6%, preferably 0.1 to 3%. The total concentration of these further constituents is in the range from 0% to 10%, preferably 0.1% to 6%, based on the mixture as a whole. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethylpiperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I are mixed with one or more further compounds and optionally with one or more additives. The further compounds are preferably selected from the compounds of the formula II, as indicated above, and optionally one or more further compounds.

In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 µm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_\| - \epsilon_\perp)$, while $\epsilon_{average}$ is $(\epsilon_\| + 2\epsilon_\perp)/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The term threshold voltage in the present application refers to the optical threshold and is quoted for 10% relative contrast ($V_{10}$), and the term saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck Ltd., Japan.

The test cells for the determination of $\Delta\varepsilon$ have a cell thickness of approximately 20 µm. The electrode is a circular ITO electrode having an area of 1.13 cm² and a guard ring. The orientation layers are SE-1211 from Nissan Chemicals, Japan, for homeotropic orientation ($\varepsilon\|$) and polyimide AL-1054 from Japan Synthetic Rubber, Japan, for homogeneous orientation ($\varepsilon\perp$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast respectively.

The liquid-crystalline media are investigated with respect to their properties in the microwave frequency range as described in A. Penirschke et al. "Cavity Perturbation Method for Characterization of Liquid Crystals up to 35 GHz", 34th European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an inner diameter of 0.5 mm and an outer diameter of 0.78 mm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the frequency depending response of the cavity is recorded using a commercial vector network analyser (N5227A PNA Microwave Network Analyzer, Keysight Technologies Inc. USA. For other frequencies, the dimensions of the cavity are adapted correspondingly.

The change in the resonance frequency and the Q factor between the measurement with the capillary filled with the liquid crystal and the measurement without the capillary filled with the liquid crystal is used to deter-mine the dielectric constant and the loss angle at the corresponding target frequency by means of equations 10 and 11 in the above-mentioned publication A. Penirschke et al., 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla.

The dielectric anisotropy in the microwave region is defined as $$\Delta\varepsilon_r = (\varepsilon_{r,\|} - \varepsilon_{r,\perp}).$$

The tunability ($\tau$) is defined as $$\tau = (\Delta\varepsilon_r/\varepsilon_{r,\|}).$$

The material quality (rt) is defined as $$\eta = (\tau/\tan\delta_{\varepsilon r,max}),$$

with the maximum dielectric loss factor $\tan\delta_{\varepsilon r,max}$:

$$\tan\delta_{\varepsilon r,max} = \max.\{\tan\delta_{\varepsilon r,\perp}; \tan\delta_{\varepsilon r,\|}\}$$

which arises from the maximum value of the measured values for $\tan\delta_{\varepsilon r}$.

The material quality ($\eta$) of the preferred liquid-crystal materials is 6 or more, preferably 7 or more, preferably 10 or more, preferably 15 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

The liquid-crystal media according to the invention preferably have nematic phases of in each case at least from -20° C. to 80° C., preferably from -30° C. to 85° C. and very particularly preferably from -40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 µm and in bulk mixtures for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The $\Delta\varepsilon$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm ($Na^D$) and 20° C., is preferably in the range of 0.20 to 0.90, more preferably in the range of 0.25 to 0.90, even more preferably in the range of 0.30 to 0.85 and very particularly preferably in the range of 0.35 or to 0.80.

In a preferred embodiment of the present application, the $\Delta n$ of the liquid-crystal media in accordance with the present invention is preferably 0.50 or more, more preferably 0.55 or more.

Furthermore, the liquid-crystal media according to the invention are characterised by high anisotropies in the microwave region. The birefringence is, for example, preferably 0.14 or more, particularly preferably 0.15 or more, particularly preferably 0.20 or more, particularly preferably 0.25 or more and very particularly preferably 0.30 or more, at about 19 GHz. In addition, the birefringence is preferably 0.80 or less.

The liquid crystals employed are either single substances or mixtures. They preferably have a nematic phase.

In the present application, the term compounds means both one compound and a plurality of compounds, unless expressly stated otherwise.

Preferred components which comprise a liquid-crystal medium or at least one compound in accordance with the invention are phase shifters, varactors, antenna arrays (for example for radio, mobile communications, micro-wave/radar and other data transmission), a tunable metamaterial structure, matching networks, tunable filters, varactors and others. Preference is given to components for high-frequency technology, as defined above. Preference is also given to components which can be modulated by different applied electrical voltages. Very particularly preferred components are tunable phase shifters. In preferred embodiments, a plurality of phase shifters are functionally connected, giving, for example, a phase-controlled group antenna, generally referred to as 'phased array' antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable or passive transmitting or receiving antenna for high frequencies (for example gigahertz region).

The antenna beam of phased-array antennae according to the invention can be steered over a wide angular region.

Preferred applications are radar installations and data transmission equipment on non-mobile terminals or manned or unmanned vehicles from the automobile, shipping, aircraft, space travel and satellite technology areas.

For the production of suitable components for high-frequency technology, in particular suitable phase shifters, a liquid-crystalline medium according to the invention is typically introduced into rectangular cavities having a thickness of less than 1 mm, a width of several millimetres and a length of several centimetres. The cavities have opposing electrodes mounted along two long sides. Such arrangements are familiar to the person skilled in the art. Through application of a variable voltage, the dielectric properties of the liquid-crystalline medium can be tuned during operation of the antenna in order to set different frequencies or directions of an antenna.

The expression "halogen" or "halogenated" stands for F, Cl, Br and I, particularly for F and Cl and in particular for F. A halogenated alkyl radical therefore preferably means a chlorinated or fluorinated alkyl radical.

The expression "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The expression "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The expression "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The expression "fluorinated alkyl radical" preferably encompasses mono- or polyfluorinated radicals. Perfluorinated radicals are included. Preference is given to $CF_3$, $CH_2CF_3$, $CH_2CHF_2$, $CHF_2$, $CH_2F$, $CHFCF_3$ and $CF_2CHFCF_3$, particularly preferably $CF_3$.

The expression "fluorinated alkoxy radical" encompasses mono- or polyfluorinated radicals. Perfluorinated radicals are preferred. Particular preference is given to the $OCF_3$ radical.

The expression "alk(en/yn)yl groups, in which one or more "—$CH_2$—" groups may be replaced by —O—" preferably relates to groups of this type in which a non-terminal $CH_2$ group is replaced. OH groups are included in the general meaning.

The expression "substituted cycloalkyl" encompasses cycloalkyl which is mono- or polysubstituted by alkyl, in particular alkyl having 1 to 8 carbon atoms.

The expression "substituted phenyl" encompasses phenyl which is mono- or polysubstituted by a group defined like $R^1$, in particular phenyl which is substituted by F, Cl, alkyl or alkoxy.

In the present application, high-frequency technology means applications having frequencies in the range from 1 MHz to 10 THz, preferably from 1 GHz to 3 THz, more preferably from 2 GHz to 1 THz, particularly preferably from 5 to 300 GHz. The application is preferably in the microwave spectrum or adjacent regions which are suitable for message transmission, in which phased-array modules can be used in transmitting or receiving antennae.

The liquid-crystal media according to the invention consist of one or more compounds, preferably 2 to 30, more preferably 3 to 20 and very preferably 3 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for R$^{1*}$, R$^{2*}$, L$^{1*}$, L$^{2*}$, L$^{3*}$ | R$^{1*}$ | R$^{2*}$ | L$^{1*}$ | L$^{2*}$ |
|---|---|---|---|---|
| nm | C$_n$H$_{2n+1}$ | C$_m$H$_{2m+1}$ | H | H |
| nOm | C$_n$H$_{2n+1}$ | OC$_m$H$_{2m+1}$ | H | H |
| nO•m | OC$_n$H$_{2n+1}$ | C$_m$H$_{2m+1}$ | H | H |
| n | C$_n$H$_{2n+1}$ | CN | H | H |
| nN•F | C$_n$H$_{2n+1}$ | CN | F | H |
| nN•F•F | C$_n$H$_{2n+1}$ | CN | F | F |
| nF | C$_n$H$_{2n+1}$ | F | H | H |
| nCl | C$_n$H$_{2n+1}$ | Cl | H | H |
| nOF | OC$_n$H$_{2n+1}$ | F | H | H |
| nF•F | C$_n$H$_{2n+1}$ | F | F | H |
| nF•F•F | C$_n$H$_{2n+1}$ | F | F | F |
| nOCF$_3$ | C$_n$H$_{2n+1}$ | OCF$_3$ | H | H |
| nOCF$_3$•F | C$_n$H$_{2n+1}$ | OCF$_3$ | F | H |
| n-Vm | C$_n$H$_{2n+1}$ | —CH=CH—C$_m$H$_{2m+1}$ | H | H |
| nV—Vm | C$_n$H$_{2n+1}$—CH=CH— | —CH=CH—C$_m$H$_{2m+1}$ | H | H |

Suitable mixture components can be found in Tables A and B.

TABLE A

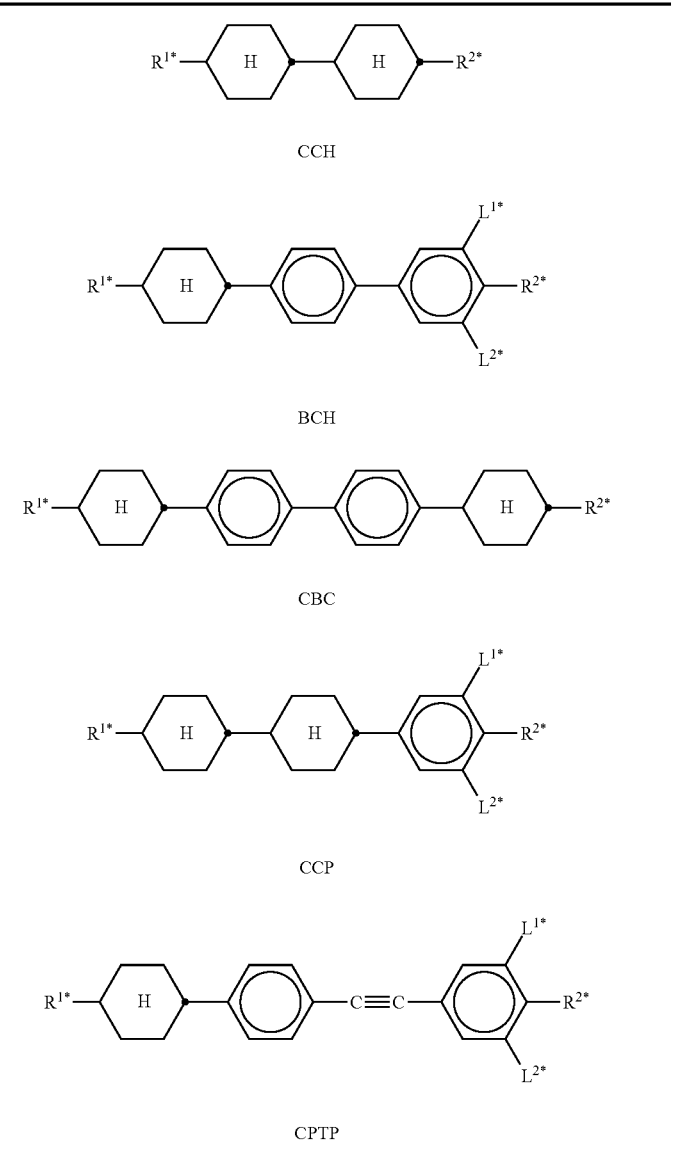

CCH

BCH

CBC

CCP

CPTP

TABLE A-continued
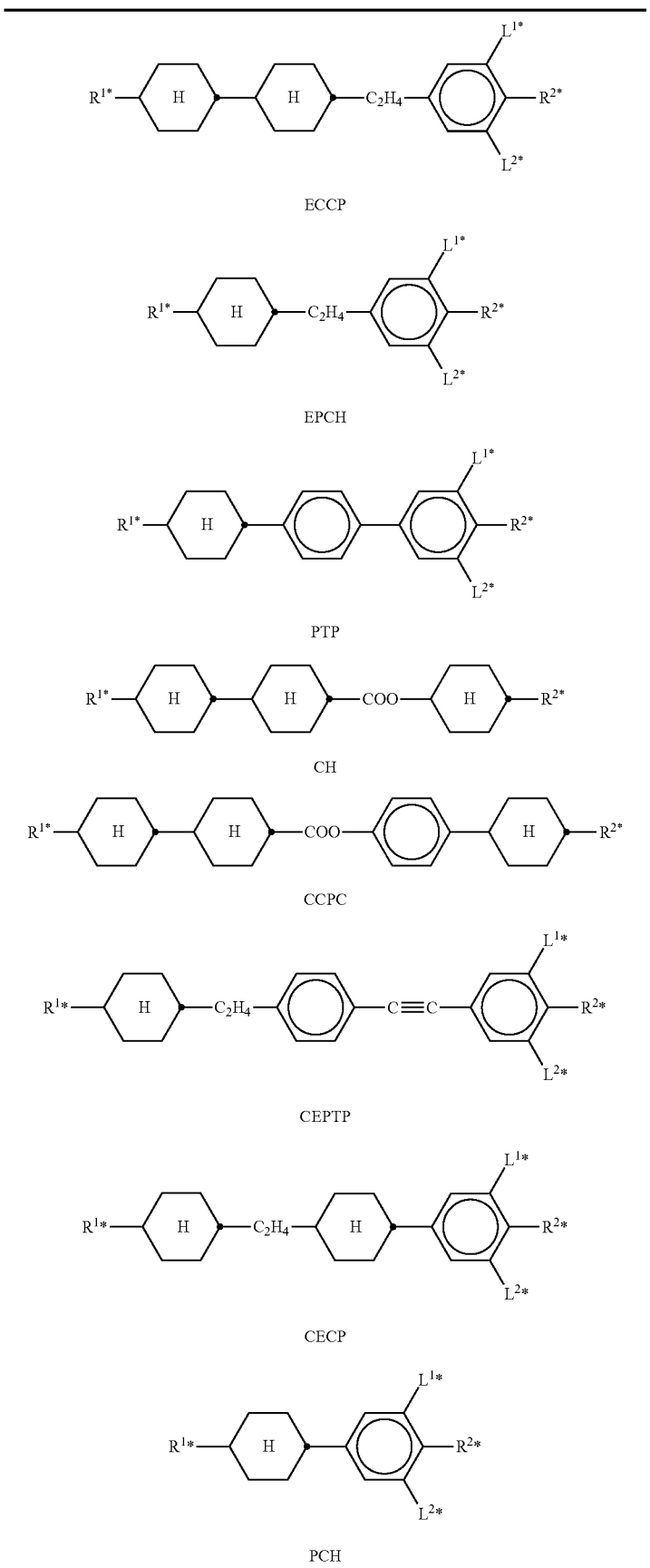

TABLE A-continued
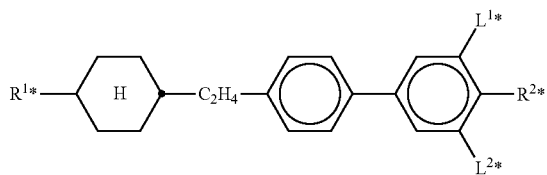
BECH
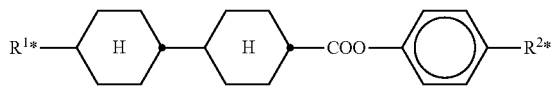
CP
TABLE B
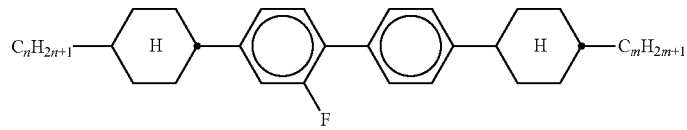
CBC-nmF
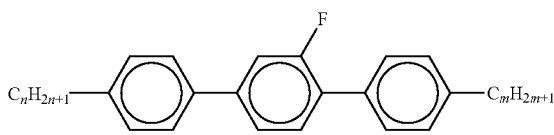
PGP-n-m
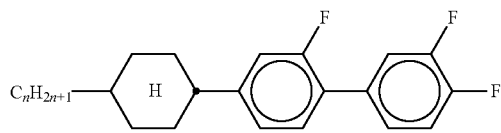
CGG-n-F
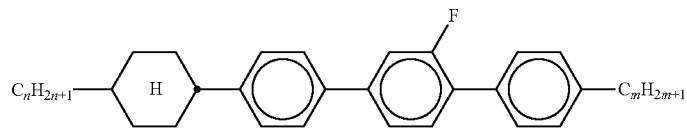
CPGP-n-m
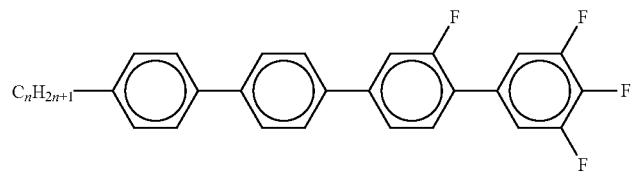
PPGU-n-F
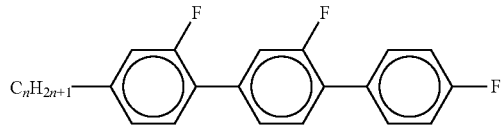
GGP-n-F TABLE B-continued
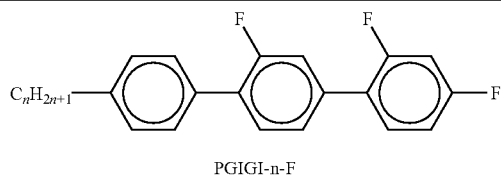
PGIGI-n-F
Table C indicates possible chiral dopants which are generally added to the mixtures according to the invention. The mixtures preferably comprise 0-10% by weight, in particular 0.001-5% by weight and particularly preferably 0.001-3% by weight, of chiral dopants.
TABLE C
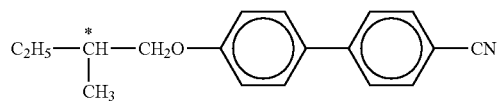
C 15
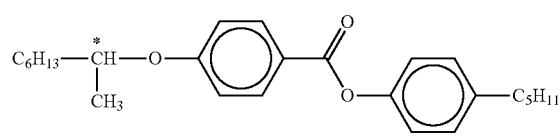
CM 21
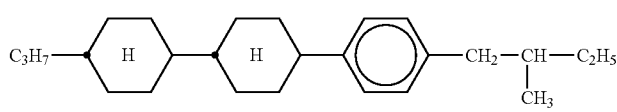
CM 44
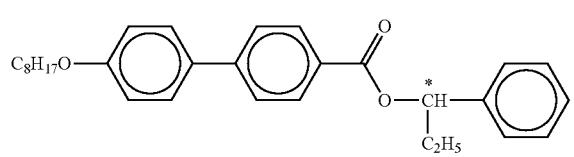
CM 47
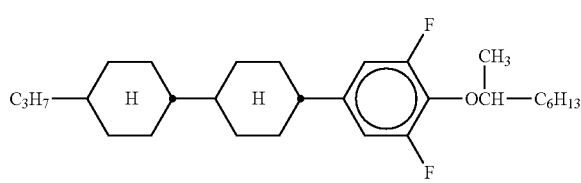
R/S-2011
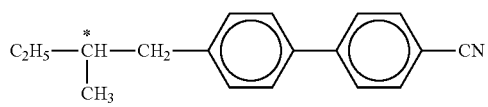
CB 15

TABLE C-continued
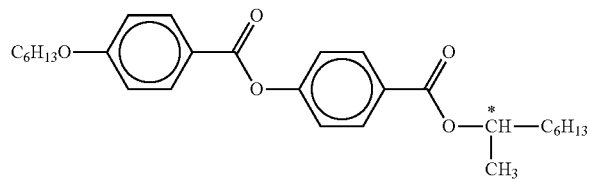
R/S-811
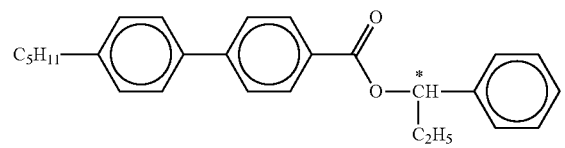
CM 45
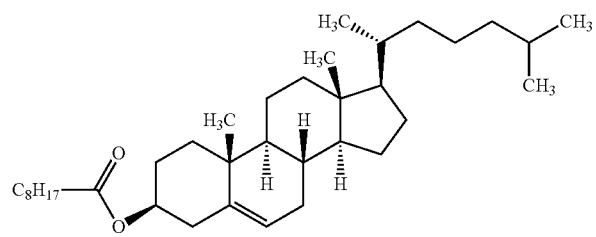
CN
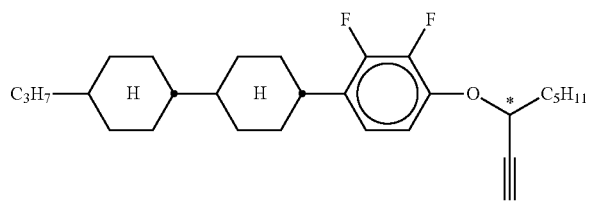
R/S-3011
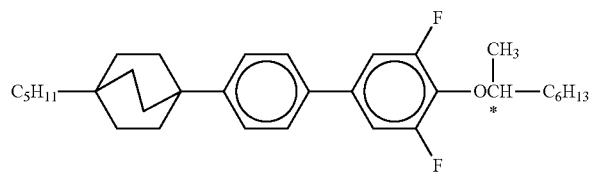
R/S-4011
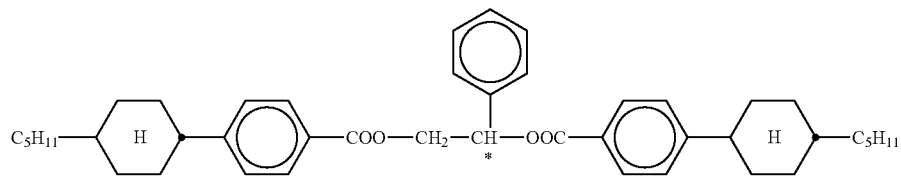
R/S-1011

TABLE C-continued
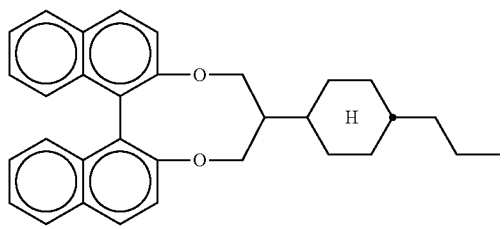
R/S-5011
TABLE D
Stabilisers which can be added, for example, to the mixtures according to the invention in amounts of 0-10% by weight are mentioned below.
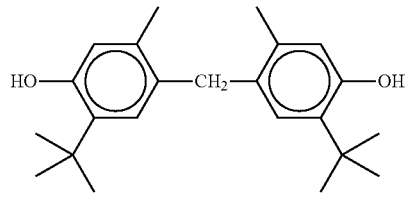
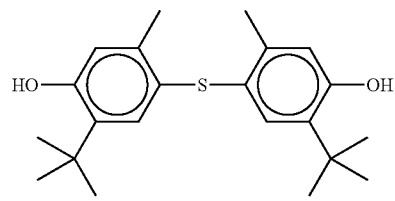
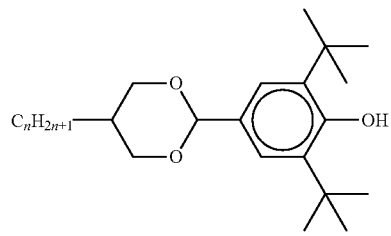
n = 1, 2, 3, 4, 5, 6 or 7
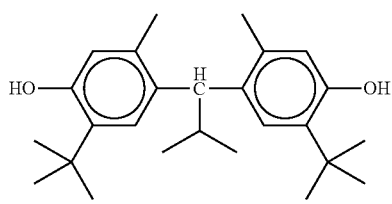
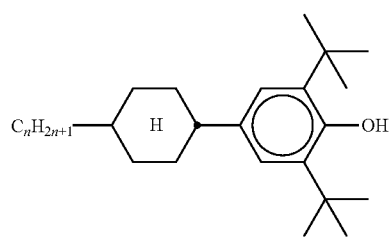
n = 1, 2, 3, 4, 5, 6 or 7

TABLE D-continued
Stabilisers which can be added, for example, to the mixtures according to the invention in amounts of 0-10% by weight are mentioned below.
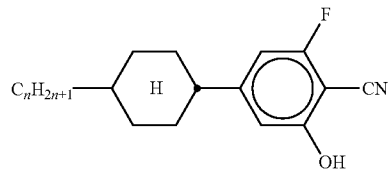
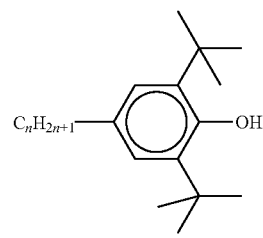
n = 1, 2, 3, 4, 5, 6 or 7
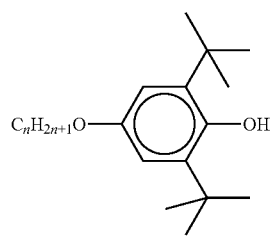
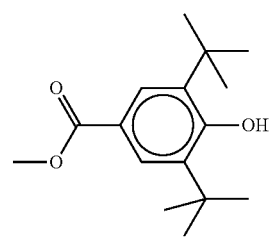
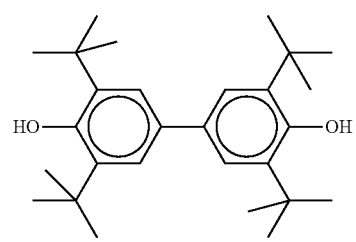
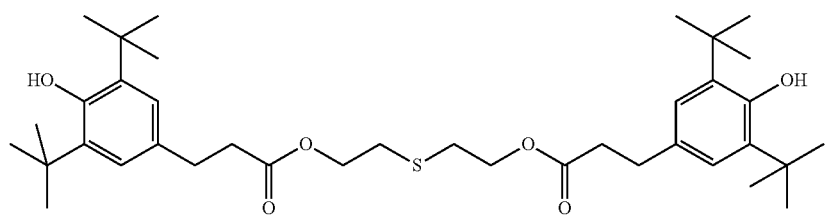 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE D-continued
Stabilisers which can be added, for example, to the mixtures according to the invention in amounts of 0-10% by weight are mentioned below.
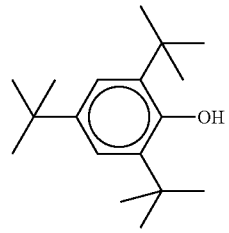
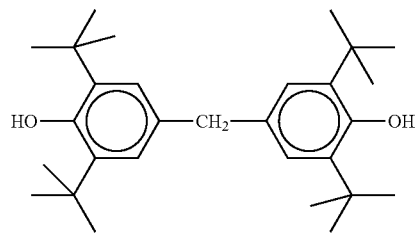
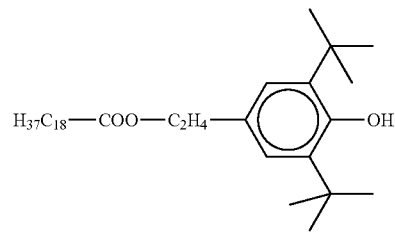
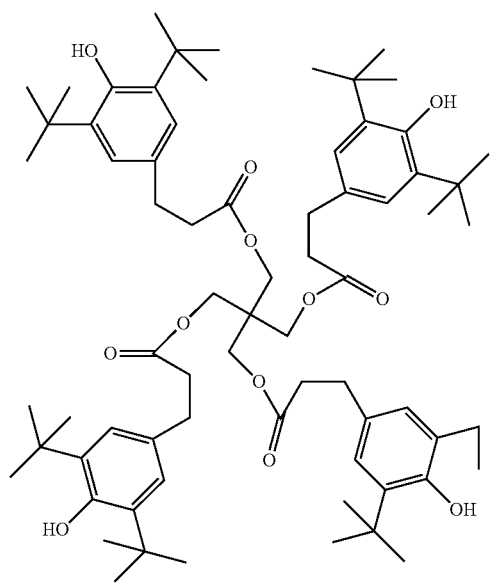 [SMILES: CCc1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE D-continued
Stabilisers which can be added, for example, to the mixtures according to the invention in amounts of 0-10% by weight are mentioned below.
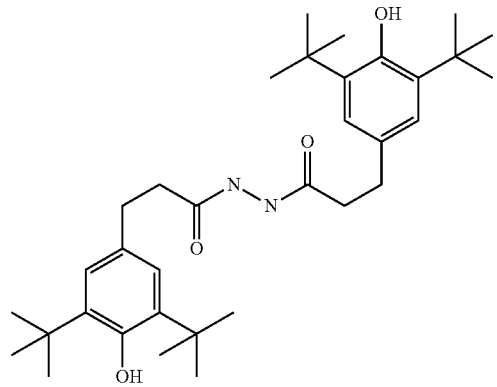 [SMILES: CC(C)(C)c1cc(CCC(=O)NNC(=O)CCc2cc(C(C)(C)C)c(O)c(C(C)(C)C)c2)cc(C(C)(C)C)c1O]
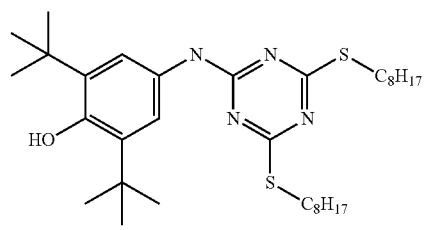
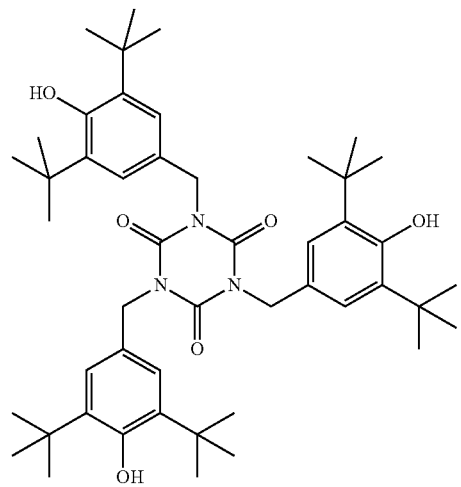 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
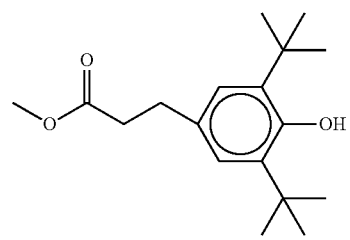

TABLE D-continued
Stabilisers which can be added, for example, to the mixtures according to the invention in amounts of 0-10% by weight are mentioned below.
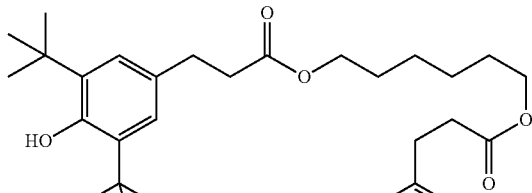
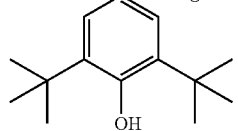
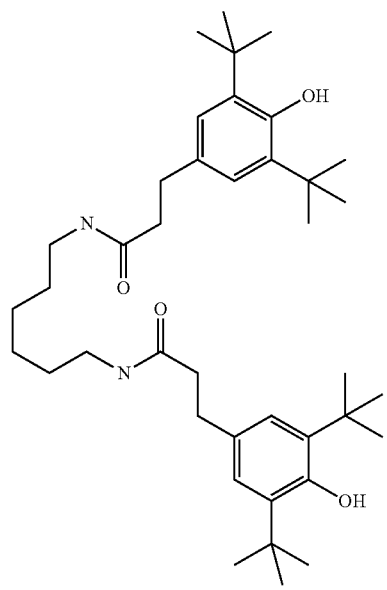 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
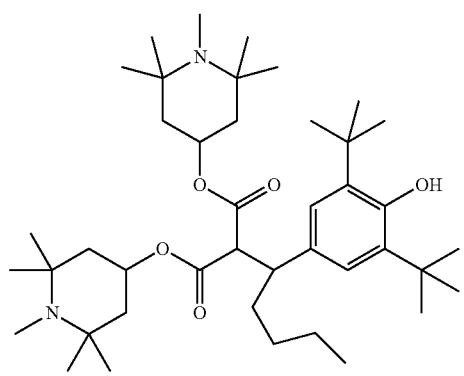 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
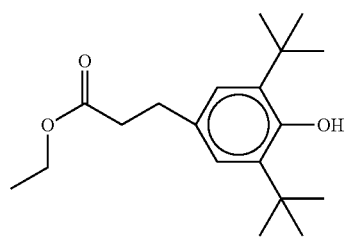

TABLE D-continued
Stabilisers which can be added, for example, to the mixtures according to the invention in amounts of 0-10% by weight are mentioned below.
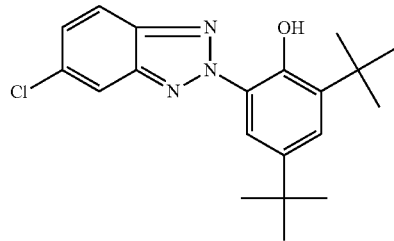 [SMILES: CC(C)(C)c1cc(-n2nc3ccc(Cl)cc3n2)c(O)c(C(C)(C)C)c1]
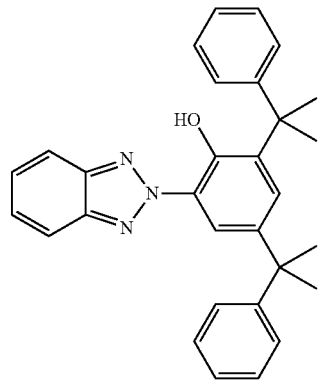 [SMILES: CC(C)(c1ccccc1)c1cc(-n2nc3ccccc3n2)c(O)c(C(C)(C)c2ccccc2)c1]
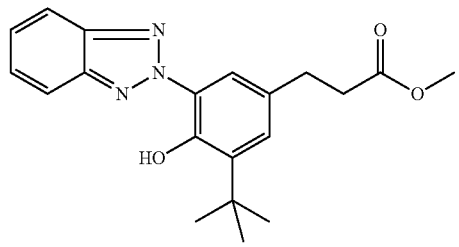 [SMILES: COC(=O)CCc1cc(-n2nc3ccccc3n2)c(O)c(C(C)(C)C)c1]
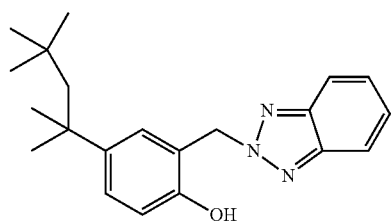 [SMILES: CC(C)(C)CC(C)(C)c1ccc(O)c(Cn2nc3ccccc3n2)c1]

TABLE D-continued
Stabilisers which can be added, for example, to the mixtures according to the invention in amounts of 0-10% by weight are mentioned below.
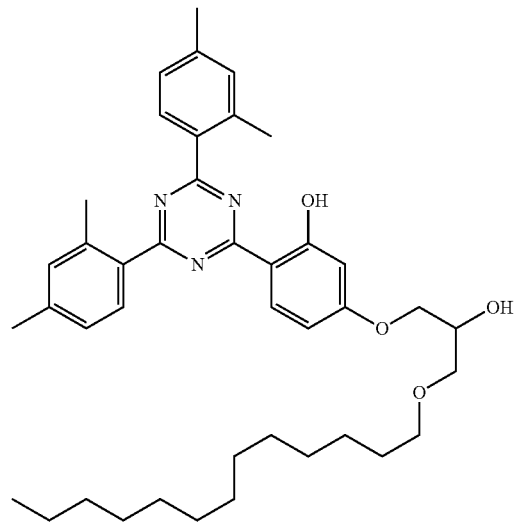 [SMILES: CCCCCCCCCCCCCOCC(O)COc1ccc(-c2nc(-c3ccc(C)cc3C)nc(-c3ccc(C)cc3C)n2)c(O)c1]
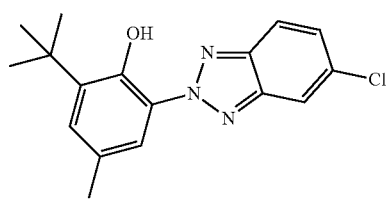 [SMILES: Cc1cc(-n2nc3ccc(Cl)cc3n2)c(O)c(C(C)(C)C)c1]
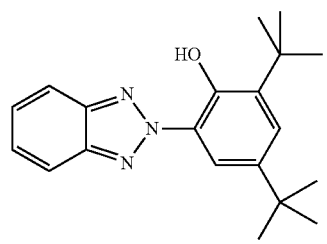 [SMILES: CC(C)(C)c1cc(-n2nc3ccccc3n2)c(O)c(C(C)(C)C)c1]
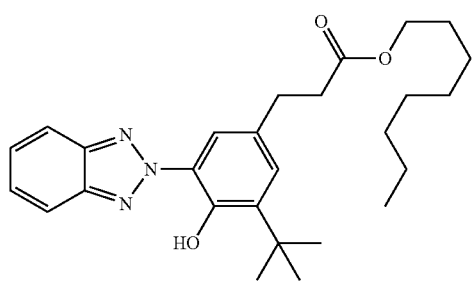 [SMILES: CCCCCCCCOC(=O)CCc1cc(-n2nc3ccccc3n2)c(O)c(C(C)(C)C)c1]
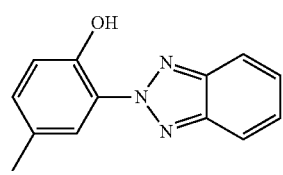 [SMILES: Cc1ccc(O)c(-n2nc3ccccc3n2)c1]

TABLE D-continued
Stabilisers which can be added, for example, to the mixtures according to the invention in amounts of 0-10% by weight are mentioned below.
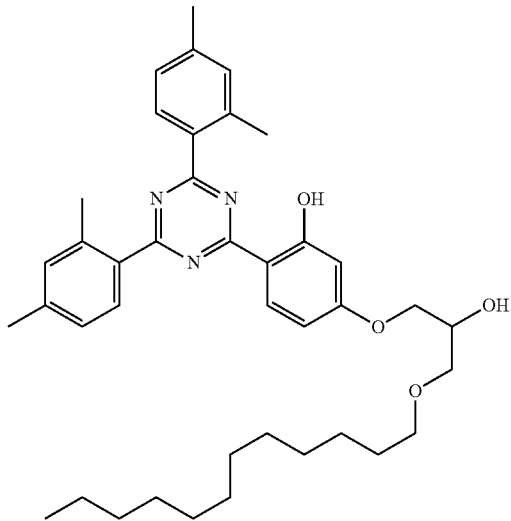 [SMILES: CCCCCCCCCCCCOCC(O)COc1ccc(-c2nc(-c3ccc(C)cc3C)nc(-c3ccc(C)cc3C)n2)c(O)c1]
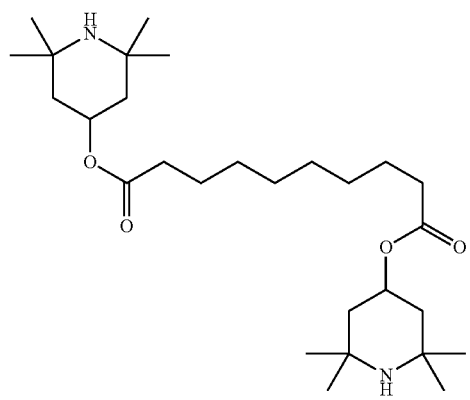
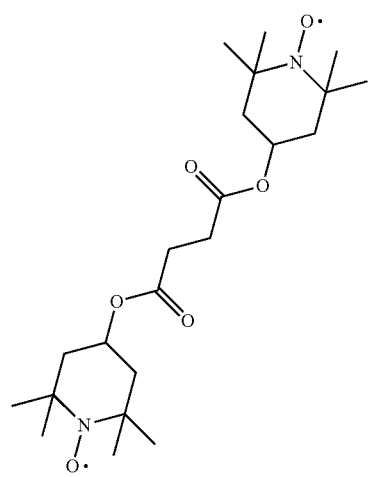

TABLE D-continued
Stabilisers which can be added, for example, to the mixtures according to the invention in amounts of 0-10% by weight are mentioned below.
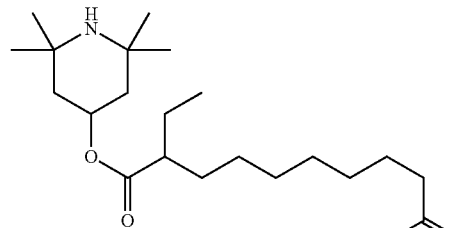
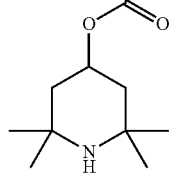
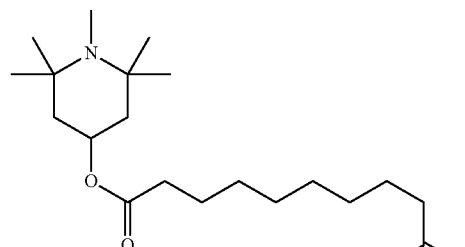
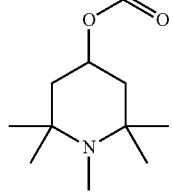
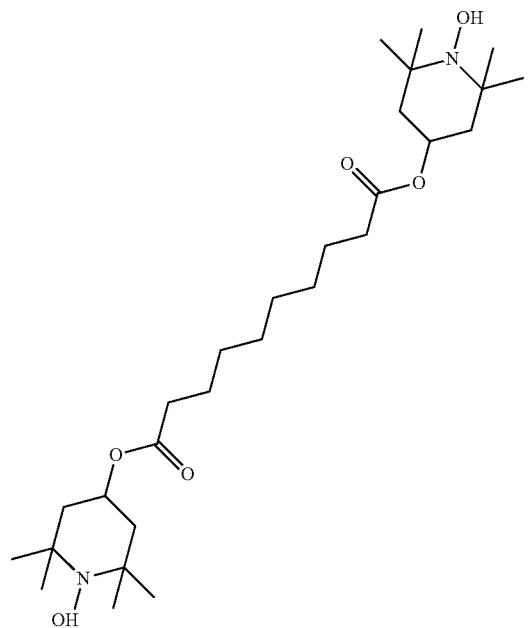

43 44
TABLE D-continued
Stabilisers which can be added, for example, to the mixtures according to the invention in amounts of 0-10% by weight are mentioned below.
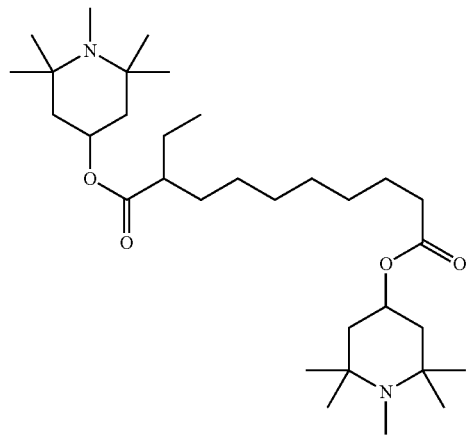
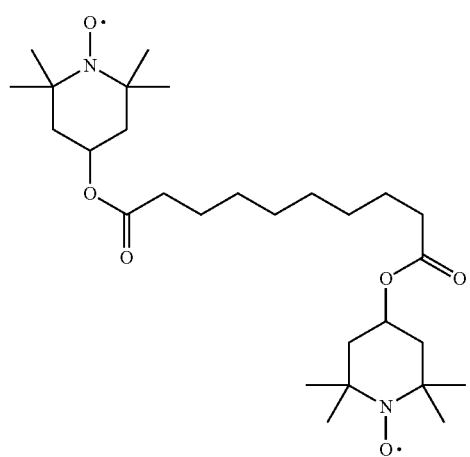
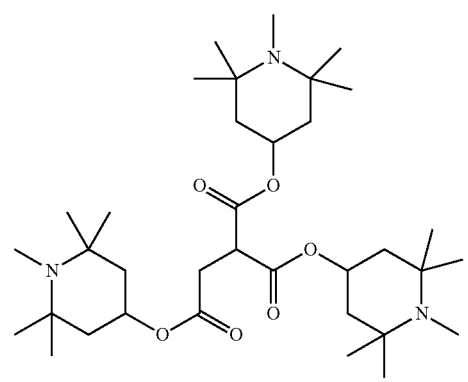

TABLE D-continued
Stabilisers which can be added, for example, to the mixtures according to the invention in amounts of 0-10% by weight are mentioned below.
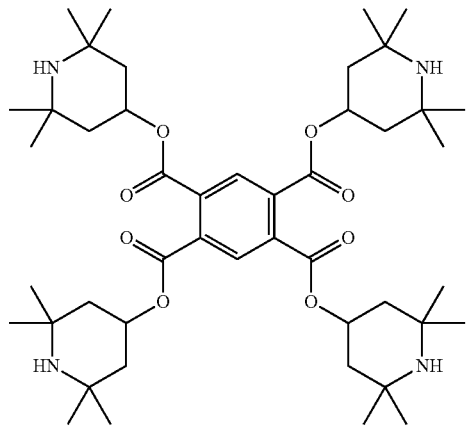
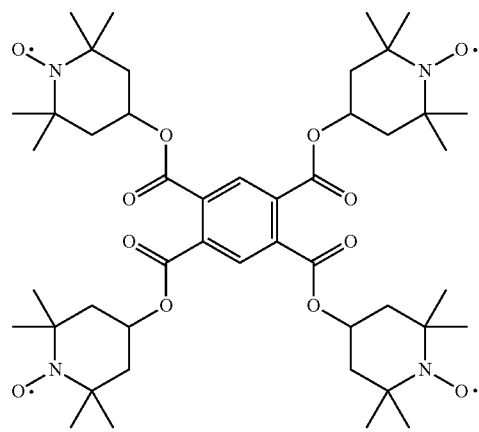
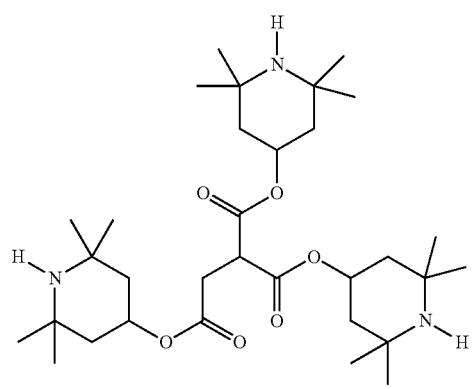 [SMILES: CC1(C)CC(OC(=O)CC(C(=O)OC2CC(C)(C)NC(C)(C)C2)C(=O)OC2CC(C)(C)NC(C)(C)C2)CC(C)(C)N1]

TABLE D-continued

Stabilisers which can be added, for example, to the mixtures according to the invention in amounts of 0-10% by weight are mentioned below.

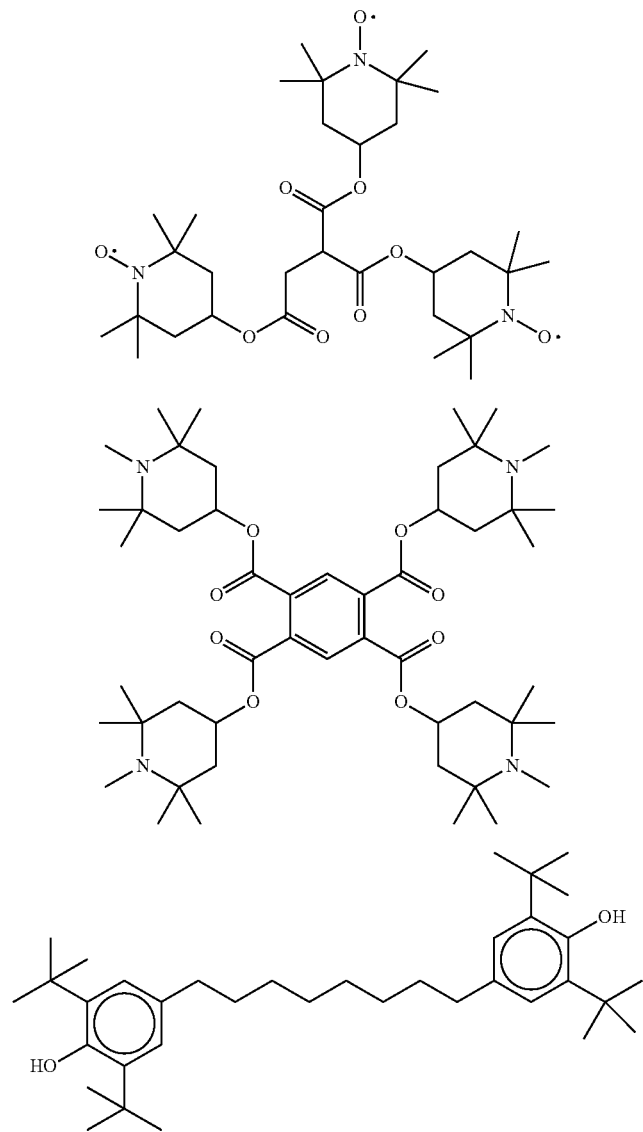

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

In the present application, unless expressly indicated otherwise, the plural form of a term denotes both the singular form and the plural form, and vice versa. Further combinations of the embodiments and variants of the invention in accordance with the description also arise from the patent claims.

SYNTHESIS EXAMPLES

Example 1: 5-[2-(2-ethyl-4-n-pentyl-phenyl)ethynyl]-1,3-difluoro-2-isothiocyanato-benzene (1)

Step 1: 4-[2-(4-bromo-2-ethyl-phenyl)ethynyl]-2,6-difluoro-aniline

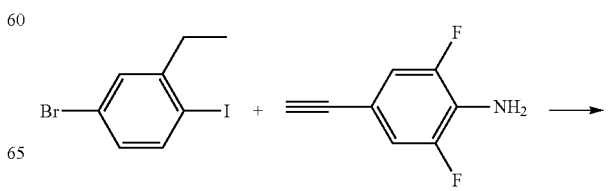

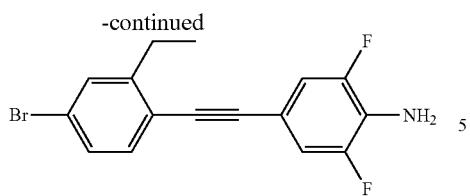

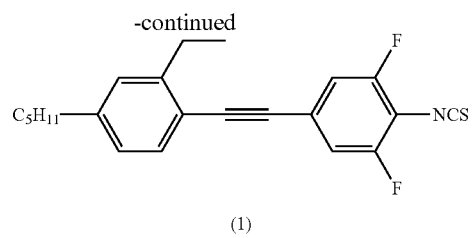

(1)

To a solution of 4-bromo-2-ethyl-1-iodobenzene (95.0 g, 0.3 mol) in triethylamine (200 mL) and THF (450 mL), Pd(PPh$_3$)$_2$Cl$_2$ (4.0 g, 5.8 mmol) and CuI (1.1 g, 5.8 mmol) are added. The resulting solution is cooled to 0° C. and a solution of 4-ethynyl-2,6-difluroaniline (45.0 g, 0.29 mol) in triethylamine (100 mL) is added dropwise. The reaction mixture is allowed to warm to ambient temperature and stirred overnight before it is filtered and concentrated under reduced pressure. The residue is purified by flash chromatography (petrol ether/toluene) to give 4-[2-(4-bromo-2-ethyl-phenyl)ethynyl]-2,6-difluoro-aniline as colourless crystals.

Step 2: 4-[2-(2-ethyl-4-n-pentyl-phenyl)ethynyl]-2, 6-difluoro-aniline

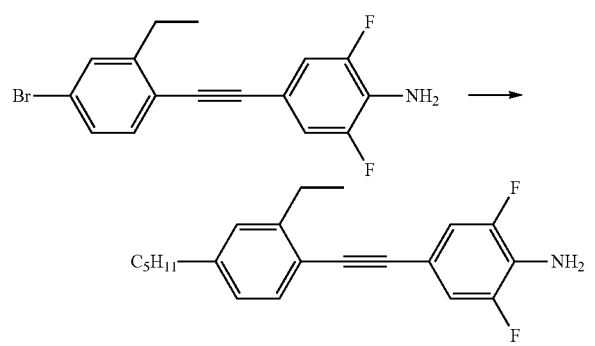

To a suspension of K$_3$PO$_4$ (40.8 g, 0.19 mol) in toluene (300 mL) and water (26 drops), Pd(dba)$_2$ (1.47 g, 2.65 mmol) and SPhos (1.10 g, 2.69 mmol) are added. The resulting mixture is stirred for 10 min at room temp. before 4-[2-(4-bromo-2-ethyl-phenyl)ethynyl]-2,6-difluoro-aniline (43.0 g, 0.13 mol), n-pentane boronic acid (22.4 g, 0.19 mol) and toluene (130 mL) are added. The reaction mixture is stirred under reflux for 20 h and treated with water. The aqueous phase is separated and extracted with methyl tert-butyl ether. The combined organic phases are washed with water and sat. NaCl solution, dried over Na$_2$SO$_4$, filtered and concentrated under vacuo. The residue is purified by flash chromatography (petrol ether/methyl tert-butyl ether) to give 4-[2-(2-ethyl-4-n-pentyl-phenyl)ethynyl]-2,6-difluoro-aniline as a yellowish oil.

Step 3: 5-[2-(2-ethyl-4-n-pentyl-phenyl)ethynyl]-1, 3-difluoro-2-isothiocyanato-benzene (1)

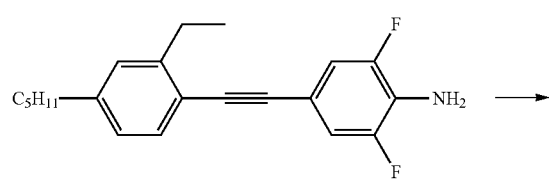

A solution of 4-[2-(2-ethyl-4-n-pentyl-phenyl)ethynyl]-2, 6-difluoro-aniline (38.8 g, 0.12 mol) in dichloromethane (490 mL) and DMF (18 mL, 0.24 mol) is treated with thiocarbonyl diimidazole (42.1 g, 0.24 mol) at room temperature. The resulting mixture is stirred overnight at the same temperature and over additional two days at 32° C. before it is filtered and concentrated under reduced pressure. The residue is purified by flash chromatography (petrol ether) recrystallization from petrol ether to give 5-[2-(2-ethyl-4-n-pentyl-phenyl)ethynyl]-1,3-difluoro-2-isothiocyanato-benzene as colourless crystals.

$^1$H NMR: δ=7.38 ppm (d, J=7.8 Hz, 1H), 7.11-7.05 (m, 3H), 7.01 (dd, J=7.8, 1.7 Hz, 1H), 2.82 (q, J=7.6 Hz, 2H), 2.63-2.55 (m, 2H), 1.68-1.57 (m, 2H), 1.41-1.25 (m, 7H), 0.93-0.86 (m, 3H);

EI-MS: 369.0.

Phase sequence: Tg −68 K 34 I

Δε: 12.1

Δn: 0.3003

Clp: −52.8° C.

γ$_1$: 112 mPa s

In analogy to Example 1 the following compounds are obtained:

Synthesis Example 2

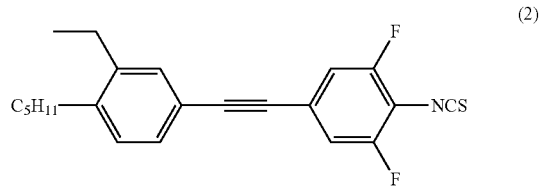

$^1$H NMR: 7.32 (d, J=1.7 Hz, 1H), 7.29-7.24 (m, 1H), 7.13 (d, J=7.8 Hz, 1H), 7.11-7.05 (m, 2H), 2.71-2.57 (m, 4H), 1.64-1.53 (m, 2H), 1.36 (hept, J=3.8, 3.2 Hz, 4H), 1.23 (t, J=7.5 Hz, 3H), 0.96-0.86 (m, 3H).

EI-MS: 369.1.

Phase sequence: Tg −59 K 51 I

Δε: 13.9

Δn: 0.2691

Clp: −84.6° C.

γ$_1$: 140 mPa s

Synthesis Example 3

(3)

C₃H₇—≡—[benzene with ethyl]—≡—[difluorobenzene]—NCS

¹H NMR: 7.38 (d, J=7.9 Hz, 1H), 7.31 (dd, J=16.7, 1.3 Hz, 1H), 7.21 (dd, J=7.9, 1.6 Hz, 1H), 7.11-7.05 (m, 2H), 2.80 (q, J=7.6 Hz, 2H), 2.40 (t, J=7.0 Hz, 2H), 1.64 (h, J=7.2 Hz, 2H), 1.27 (t, J=7.6 Hz, 3H), 1.06 (t, J=7.4 Hz, 3H).
EI-MS: 365.1.
Phase sequence: K 85 I
Δε: 12.5
Δn: 0.4024
Clp: −34.1° C.
γ₁: 288 m Pa s

Synthesis Example 4

(4)

C₃H₇—≡—[benzene with ethyl]—≡—[difluorobenzene]—NCS

¹H NMR: 7.34 (d, J=8.1 Hz, 2H), 7.28-7.22 (m, 2H), 7.13-7.04 (m, 2H), 2.78 (q, J=7.5 Hz, 2H), 2.44 (t, J=7.0 Hz, 2H), 1.65 (h, J=7.2 Hz, 2H), 1.24 (t, J=7.6 Hz, 3H), 1.06 (t, J=7.4 Hz, 3H).
EI-MS: 365.2.
Phase sequence: K 77 I
Δε: 16.3
Δn: 0.3964
Clp: −21.0° C.
γ₁: 229 m Pa s

Synthesis Example 5

(5)

C₃H₇—≡—[benzene with cyclopropyl]—≡—[difluorobenzene]—NCS

¹H NMR: 7.40 (d, J=7.9 Hz, 1H), 7.29 (s, 1H), 7.19 (dd, J=7.9, 1.6 Hz, 1H), 7.16-7.09 (m, 2H), 6.92 (d, J=1.5 Hz, 1H), 2.42 (t, J=7.1 Hz, 2H), 2.31 (ddd, J=13.6, 8.5, 5.2 Hz, 1H), 1.66 (h, J=7.3 Hz, 2H), 1.28 (s, 2H), 1.07 (t, J=7.3 Hz, 5H), 0.79 (dt, J=6.7, 4.8 Hz, 2H).
EI-MS: 377.0.
Phase sequence: K 110 I

Synthesis Example 6

(6)

C₅H₁₁—[benzene with cyclopropyl]—≡—[difluorobenzene]—NCS

¹H NMR: 7.32-7.26 (m, 2H), 7.06-7.00 (m, 1H), 6.89 (dd, J=7.9, 1.6 Hz, 1H), 6.60 (d, J=1.8 Hz, 1H), 2.53-2.43 (m, 2H), 2.27-2.18 (m, 1H), 1.56-1.45 (m, 2H), 1.23 (ddt, J=13.5, 9.6, 6.0 Hz, 4H), 1.01-0.91 (m, 2H), 0.85-0.75 (m, 3H), 0.68 (dtd, J=6.4, 4.7, 1.4 Hz, 2H).
EI-MS: 381.1.
Phase sequence: K 63 I
Δε: 10.9
Δn: 0.2807
Clp: −70.1° C.
γ₁: 203 m Pa s

Synthesis Example 7

(7)

C₅H₁₁—[benzene with methyl]—≡—[difluorobenzene]—NCS

¹H NMR: 7.40 (d, J=7.8 Hz, 1H), 7.15-7.07 (m, 3H), 7.03 (dd, J=7.8, 1.7 Hz, 1H), 2.65-2.57 (m, 2H), 2.49 (s, 3H), 1.69-1.58 (m, 2H), 1.42-1.28 (m, 4H), 0.95-0.90 (m, 3H).
EI-MS: 355.0.
Phase sequence: Tg −67 K 40 N (−23.9) I
Δε: 14.9
Δn: 0.3366
Clp: −7.4° C.
γ₁: 133 mPa s

Synthesis Example 8

(8)

C₅H₁₁—[benzene with methyl]—≡—[difluorobenzene]—NCS

¹H NMR: 7.29 (d, J=1.7 Hz, 1H), 7.27 (dd, J=7.9, 1.6 Hz, 1H), 7.12 (d, J=7.7 Hz, 1H), 7.10-7.07 (m, 2H), 2.63-2.56 (m, 2H), 2.30 (s, 3H), 1.62-1.54 (m, 2H), 1.36 (h, J=3.7 Hz, 4H), 0.96-0.87 (m, 3H).
EI-MS: 355.1.
Phase sequence: K 44 I
Δε: 16.8
Δn: 0.3172
Clp: −28.2° C.
γ₁: 152 mPa s Synthesis Example 9

(9)

¹H NMR: 7.11-7.06 (m, 2H), 6.90 (s, 2H), 2.56-2.51 (m, 2H), 2.45 (s, 6H), 1.64-1.55 (m, 2H), 1.32 (ddt, J=11.3, 8.2, 5.4 Hz, 4H), 0.90 (t, J=7.0 Hz, 3H).
EI-MS: 369.1.
Phase sequence: K 66 I
Δε: 11.2
Δn: 0.3051
Clp: −47.6° C.
γ₁: 175 mPa s Synthesis Example 10

(10)

¹H NMR: 7.24 (s, 1H), 7.10-7.04 (m, 2H), 6.99 (s, 1H), 2.60-2.52 (m, 2H), 2.41 (s, 3H), 2.25 (s, 3H), 1.55 (ddt, J=10.0, 7.1, 5.1 Hz, 2H), 1.35 (dq, J=7.2, 3.5 Hz, 4H), 0.94-0.88 (m, 3H).
EI-MS: 379.1.
Phase sequence: K 63 I
Δε: 13.1
Δn: 0.2883
Clp: −63.8° C.
γ₁: 212 mPa s Synthesis Example 11

Synthesis Example 12

Synthesis Example 13

Synthesis Example 14

Synthesis Example 15

Synthesis Example 16

Synthesis Example 17
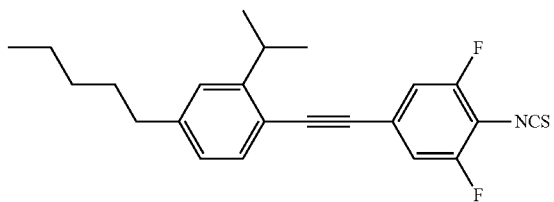
Synthesis Example 22
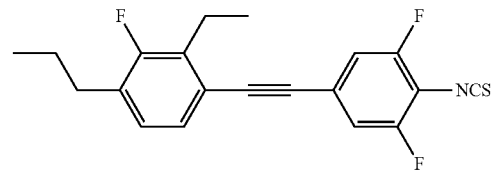
Synthesis Example 18
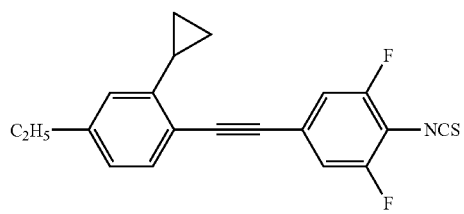
Synthesis Example 23
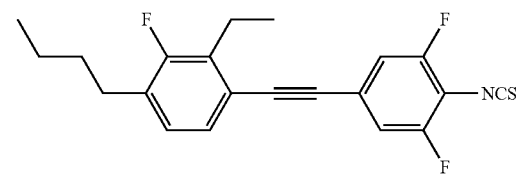
Synthesis Example 19
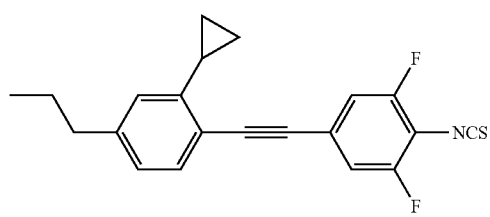
Synthesis Example 24
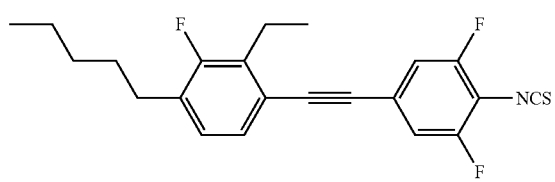
Synthesis Example 20
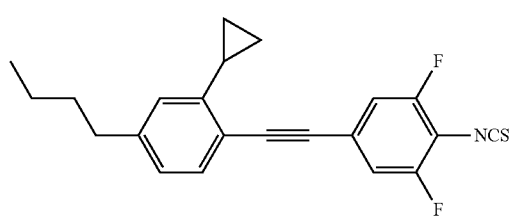
Synthesis Example 25
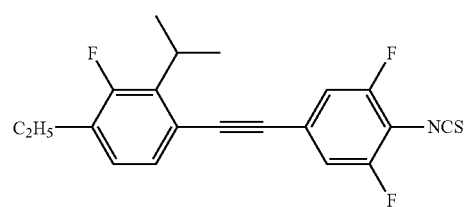
Synthesis Example 21
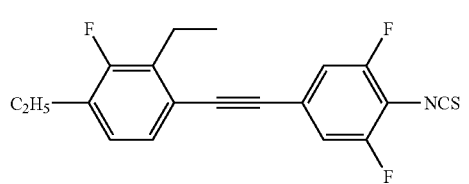
Synthesis Example 26
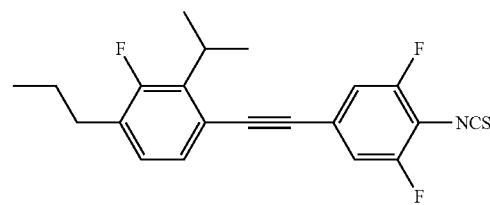

Synthesis Example 27
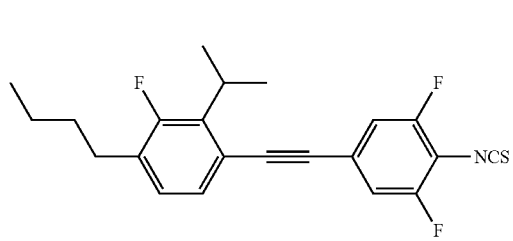
Synthesis Example 28
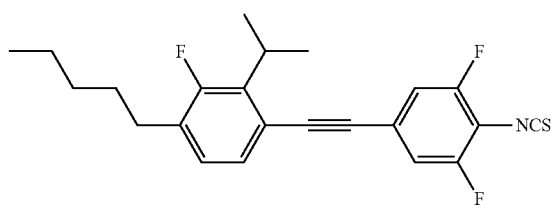
Synthesis Example 29
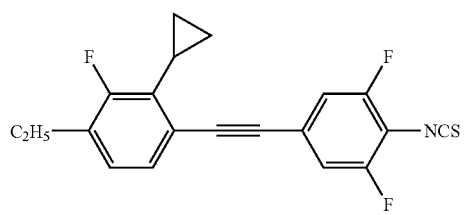
Synthesis Example 30
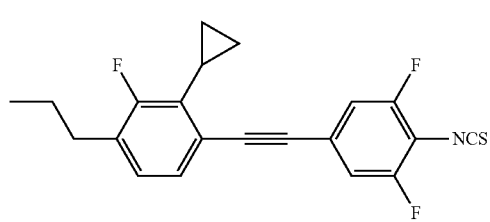
Synthesis Example 31
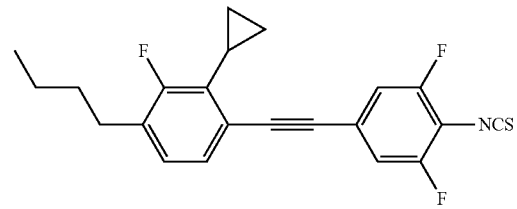
Synthesis Example 32
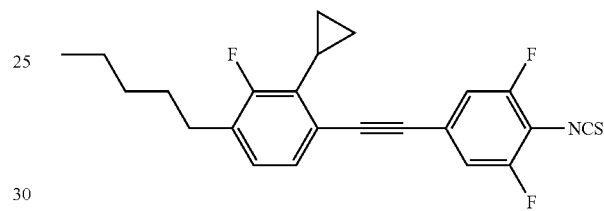
Synthesis Example 33
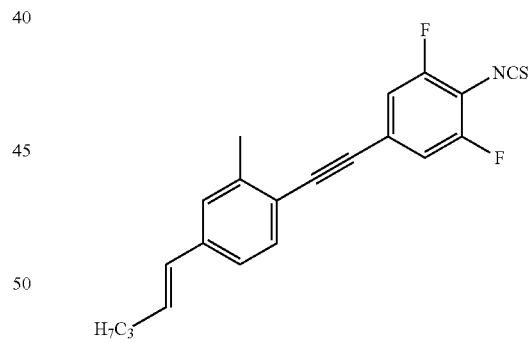
$^1$H NMR (400 MHz, Chloroform-d) δ 7.21 (d, J=1.6 Hz, 1H), 7.16 (dd, J=7.9, 1.7 Hz, 1H), 7.12-7.05 (m, 2H), 6.41-6.21 (m, 2H), 2.46 (s, 3H), 2.20 (td, J=7.3, 5.9 Hz, 2H), 1.55-1.45 (m, 2H), 0.96 (t, J=7.4 Hz, 3H).
EI-MS: 353.1
Phase sequence: K 49 N 69.2 I
Δε: 17.1
Δn: 0.4378
Clp: 68.4° C.
$\gamma_1$: 334 m Pa s

Synthesis Example 34

¹H NMR (500 MHz, Chloroform-d) δ 7.33 (d, J=7.9 Hz, 1H), 7.17-7.06 (m, 2H), 7.06-6.97 (m, 2H), 6.34-6.15 (m, 2H), 2.75 (q, J=7.6 Hz, 2H), 2.19-2.08 (m, 2H), 1.53-1.37 (m, 4H), 1.22 (t, J=7.6 Hz, 3H), 0.89 (t, J=7.4 Hz, 3H).

Phase sequence: K 73 I
Δε: 14.5
Δn: 0.4197
Clp: 13.2° C.

Synthesis Example 35

¹H NMR (400 MHz, Chloroform-d) δ 7.42 (d, J=7.9 Hz, 1H), 7.30 (s, 2H), 7.14-7.04 (m, 2H), 6.66-6.55 (m, 1H), 6.17 (dt, J=15.5, 7.0 Hz, 1H), 2.69 (q, J=7.5 Hz, 2H), 2.23 (qd, J=7.1, 1.5 Hz, 2H), 1.52 (h, J=7.3 Hz, 2H), 1.21 (t, J=7.5 Hz, 3H), 0.97 (t, J=7.3 Hz, 3H). EI-MS: 367.2

Phase sequence: K 65 I
Δε: 15.9
Δn: 0.3534
Clp: −26.7° C.
γ₁: 271 mPa s

Synthesis Example 36

¹H NMR (400 MHz, Chloroform-d) δ 7.18 (d, J=1.6 Hz, 2H), 7.13-7.06 (m, 2H), 7.05 (d, J=1.7 Hz, 1H), 2.62 (q, J=7.6 Hz, 4H), 1.24 (t, J=7.6 Hz, 6H). EI-MS: 327.1

Phase sequence: K 113 I
Δε: 8.4
Δn: 0.1764
Clp: −194.8° C.
γ₁: 36 mPa s

Synthesis Example 37

Synthesis Example 38

Use Examples

A nematic liquid-crystal medium N-1 having the composition and properties as indicated in the following table is prepared.

| No. | Composition Compound Abbreviation | | Physical properties | |
|---|---|---|---|---|
| 1 | BCH-3F•F | 12.0% | T(N, I) = | 92° C. |
| 2 | BCH-5F•F | 10.0% | Δn (20° C., 589.3 nm) = | 0.0969 |
| 3 | ECCP-30CF3 | 5.0% | Δε (20° C., 1 kHz) = | 5.2 |
| 4 | ECCP-50CF3 | 5.0% | $\gamma_1$ (20° C.) = | 134 mPa · s |
| 5 | CBC-33F | 2.0% | | |
| 6 | CBC-53F | 2.0% | | |
| 7 | CBC-55F | 2.0% | | |
| 8 | PCH-6F | 8.0% | | |
| 9 | PCH-7F | 6.0% | | |
| 10 | CCP-20CF3 | 8.0% | | |
| 11 | CCP-30CF3 | 12.0% | | |
| 12 | CCP-40CF3 | 7.0% | | |
| 13 | CCP-50CF3 | 11.0% | | |
| 14 | PCH-5F | 10.0% | | |
| Σ | | 100.0% | | |

Mixture Examples

The Mixture Example M-1 is prepared from liquid-crystal host material N-1 above and the compound 1 of Synthesis Example 1 and consists of 90% by weight of N-1 and 10% by weight of compound 1. Accordingly, the Mixture Examples M-2 to M-10 and M-33 to M-35 are each prepared from liquid-crystal host material N-1 and compounds 2 to 10 and 33 to 35 of Synthesis Examples 2 to 10 and 33 to 35, respectively, and also consist of 90% of N-1 and 10% of compound 2 to 10 and 33 to 35, respectively.

TABLE 1

Properties of mixtures M-1 to M-10 and N-1 (comparison) at 19 GHz (20° C.)

| Mixture | $\varepsilon_{r,\parallel}$ | $\tan \delta_{\varepsilon\, r,\parallel}$ | $\varepsilon_{r,\perp}$ | $\tan \delta_{\varepsilon\, r,\perp}$ | τ | η |
|---|---|---|---|---|---|---|
| M-1 | 2.5453 | 0.0050 | 2.2306 | 0.0120 | 0.1237 | 10.3 |
| M-2 | 2.5437 | 0.0051 | 2.2370 | 0.0118 | 0.1206 | 10.2 |
| M-3 | 2.5960 | 0.0048 | 2.2620 | 0.0117 | 0.1287 | 11.0 |
| M-4 | 2.5568 | 0.0052 | 2.2336 | 0.0116 | 0.1264 | 10.9 |
| M-5 | — | — | — | — | — | — |
| M-6 | 2.5513 | 0.0049 | 2.2414 | 0.0117 | 0.1215 | 10.4 |
| M-7 | 2.5865 | 0.0050 | 2.2724 | 0.0122 | 0.1215 | 10.0 |
| M-8 | 2.5787 | 0.0051 | 2.2713 | 0.0121 | 0.1192 | 9.9 |
| M-9 | 2.5849 | 0.0049 | 2.2741 | 0.0120 | 0.1203 | 10.0 |
| M-10 | 2.5708 | 0.0050 | 2.2668 | 0.0117 | 0.1183 | 10.1 |
| M-33 | 2.6260 | 0.0048 | 2.2917 | 0.0121 | 0.1273 | 10.5 |
| M-34 | 2.6191 | 0.0050 | 2.3083 | 0.0120 | 0.1186 | 9.9 |
| M-35 | 2.6042 | 0.0050 | 2.2876 | 0.0120 | 0.1216 | 10.1 |
| N-1 | 2.56 | 0.0049 | 2.29 | 0.0126 | 0.107 | 8.5 |

As can be seen from the data in Table 1, the use of a compound of formula I according to the invention results in an improvement of the material quality (η) of the medium N-1 due to a decrease of the dielectric loss.

The invention claimed is:

1. A compound of formula I-1

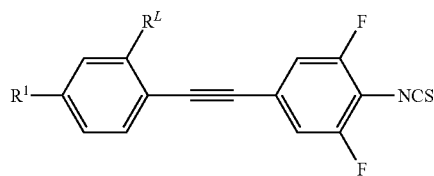

I-1 in which
$R^1$ denotes ethyl, n-propyl, n-butyl, n-pentyl, or n-hexyl,
$R^L$ denotes ethyl.

2. A method comprising including a compound of formula I-1 according to claim 1 in a liquid-crystal medium.

3. A liquid-crystal medium, comprising one or more compounds of formula I-1 according to claim 1.

4. The medium according to claim 3, where the medium additionally comprises one or more compounds of formula II

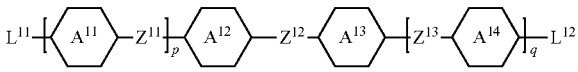

in which
$L^{11}$ denotes $R^{11}$ or $X^{11}$,
$L^{12}$ denotes $R^{12}$ or $X^{12}$,
$R^{11}$ and $R^{12}$, independently of one another, denote unfluorinated alkyl or unfluorinated alkoxy having 1 to 17, C atoms or unfluorinated alkenyl, unfluorinated alkynyl, unfluorinated alkenyloxy or unfluorinated alkoxyalkyl having 2 to 15,
$X^{11}$ and $X^{12}$, independently of one another, denote F, Cl, Br, —CN, —NCS, —SCN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, $OCF_3$, Cl, F or NCS,
p, q, independently of one another, denote 0 or 1,
$Z^{11}$ to $Z^{13}$, independently of one another, denote trans—CH=CH—, trans—CF=CF—, —C≡C— or a single bond,

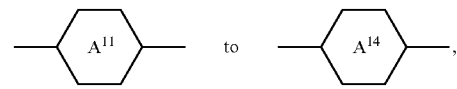

independently of one another, denote

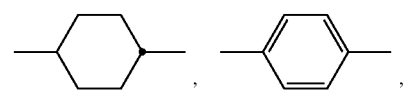

-continued

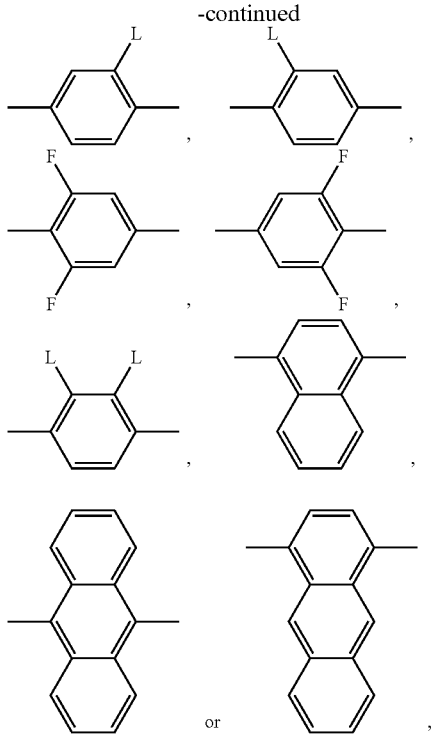

and

L on each occurrence, independently of one another, denotes methyl, unbranched alkyl having 2 to 12 C atoms, or branched alkyl, alkenyl or alkynyl having 2 to 12 C atoms, in which, independently of one another, one or more —$CH_2$— groups may also be replaced by O, or denotes $C_3$-$C_6$ cycloalkyl, $C_3$-$C_6$ cycloalkenyl, fluorinated alkyl or alkenyl, fluorinated alkoxy or alkenyloxy, F, Cl, Br, CN, NCS, SCN or $SF_5$.

5. A compound of formula

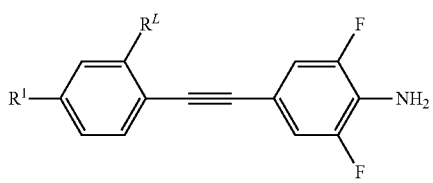

in which $R^1$ denotes ethyl, n-propyl, n-butyl, n-pentyl, or n-hexyl and $R^L$ denotes ethyl.

6. A process for the preparation of a compound according to claim 5, wherein a compound of formula I-1* is transferred into a compound of formula I-1

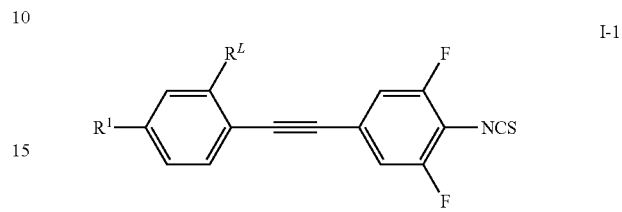

in which $R^1$ denotes ethyl, n-propyl, n-butyl, n-pentyl, or n-hexyl and $R^L$ denotes ethyl.

7. A method which comprises including a liquid-crystal medium according to claim 3 in a component for high-frequency technology.

8. A component for high-frequency technology, comprising a liquid crystal medium according to claim 3.

9. A component according to claim 8, where the component is suitable for operation in the microwave range.

10. A component according to claim 8, where the component is an LC based antenna element, a phase shifter, a tunable filter, a tunable metamaterial structure, a matching network or a varactor.

11. Microwave antenna array, comprising one or more components according to claim 8.

12. The medium of claim 4, wherein $R^{11}$ and $R^{12}$, independently of one another, unfluorinated alkyl or unfluorinated alkoxy having 3-10 C atoms.

13. The medium of claim 4, wherein $R^{11}$ and $R^{12}$, independently of one another, denote unfluorinated alkenyl, unfluorinated alkynyl, unfluorinated alkenyloxy or unfluorinated alkoxyalkyl having having 3 to 10 C atoms.

14. The medium of claim 4, wherein $X^{11}$ and $X^{12}$, independently of one another, denote $CF_3$, $OCF_3$, Cl, F or NCS.

* * * * *